United States Patent [19]
Strum et al.

[11] Patent Number: 5,842,173
[45] Date of Patent: Nov. 24, 1998

[54] COMPUTER-BASED SURGICAL SERVICES MANAGEMENT SYSTEM

[76] Inventors: David P. Strum, 1035 S. Trenton Ave.; Luis G. Vargas, 726 E. End Ave., both of Pittsburgh, Pa. 15221

[21] Appl. No.: 858,327

[22] Filed: May 19, 1997

Related U.S. Application Data

[63] Continuation of Ser. No. 323,137, Oct. 14, 1994, abandoned.

[51] Int. Cl.$^6$ ................................................. G06F 159/00
[52] U.S. Cl. .................................................. 705/1; 705/8
[58] Field of Search .............................. 395/601, 187.01, 395/200.3, 200.35, 200.5, 200.53, 683; 705/1, 8

[56] References Cited

U.S. PATENT DOCUMENTS

| | | | |
|---|---|---|---|
| 4,937,743 | 6/1990 | Rassman | 364/401 |
| 5,065,315 | 11/1991 | Garcia | 364/413.01 |
| 5,276,775 | 1/1994 | Meng | 395/55 |
| 5,289,531 | 2/1994 | Levine | 379/93 |
| 5,321,605 | 6/1994 | Chapman et al. | 364/402 |
| 5,398,336 | 3/1995 | Tantry et al. | 395/600 |

OTHER PUBLICATIONS

D. Taylor, *Object–Oriented Technology: A Manager's Guide*, Addison–Wesley Publishing Company, 1990.

Primary Examiner—Frantzy Poinvil
Attorney, Agent, or Firm—Ostrolenk, Faber, Gerb & Soffen, LLP

[57] ABSTRACT

A computer-based surgical services management system for communicating between sites of a surgical services facility including a computer workstation located at each site of the facility, a server in network communication with each workstation, and a database resident on the network. The database retains patient-specific data maintained temporarily by the workstation located at a site where a patient is located, the patient-specific data moving from site to site with the patient, and site-specific data, maintained at the site where the site-specific data is produced. The database is distributed to and contained within each workstation for editing by a user. A copy of the database is contained in each workstation and is duplicated on the server. The database is of an object-oriented design containing classes for patients, locations, resources, surgeons and anesthesiologists. Methods are assigned to each of the classes for updating information. Methods also are assigned to perform constraint propagation in the network to maintain data structure. The workstations are in a peer-to-peer relationship. A copy of the database being contained on each of the individual workstations is also contained in the server. Changes to data made on each of the workstations are duplicated on the server and are updated to the other workstations periodically.

28 Claims, 14 Drawing Sheets

FIG. 3

OR SCHEDULE
4/25/1994

| OR | TIME | SURGEON | PROCEDURE | PATIENT | AGE | ROOM | ANESTHESIA |
|---|---|---|---|---|---|---|---|
| 1 | 730 | T.Powell | Allogenic Bone Marrow Harvest | Miller, Andrew | 31 | SDSO | GENERAL |
| 2 | 730 | A.Ford | Right Thyroid Lobectomy, Possible Total Thyroidectomy | Ayres, Abigail | 23 | SDSO | GENERAL |
|   | 930 | A.Ford | Exploratory Laparotomy, Colectomy Mucous Fistula | Worth, Rebecca | 80 | SI252 | GENERAL |
|   | 1500 | Gruendel/Neeson | Needle Localization 12:30, Repair of Incisional Hernia, Excision Right Breast Mass | Reddings, Paula | 48 | SDSO | GENERAL |
| 3 | 730 | V.Schwartz | Possible Open Rotator Cuff Repair Arthroscopy Right Shoulder | Smith, Becca | 31 | SDS | GENERAL |
|   | 930 | H.Stewart | Irrigation and Debridement Dressing Change Bilaterl Legs | Bucanni, Joe | 54 | N1080 | GENERAL |
| 4 | 730 | R.Reed | Right Fronto Temporal Cranioplasty | Quinn, Melissa | 18 | N1267 | GENERAL |
|   | 1300 | C.Torrence | Baclofen Pump Revision | Small, Henrietta | 60 | N1285 | GENERAL |
|   | 1400 | C.Torrence | Placement Subcutaneous Resorvoir for Epidural Catheter | Palarino, Randolph | 74 | N1042 | GENERAL |
| 5 | 730 | H.Patterson | Right Carpal Tunnel Release | Taylor, Ralph | 27 | SDS | LOCAL |
|   | 830 | H.Patterson | Re-do Right Shoulder Acromioplasty DCR, RCR | Matthews, Scott | 42 | SDSO | GENERAL |
| 6 | 730 | M.Powell | Left Total Knee Replacement | Metcalf, Rudolph | 67 | SDSO | GENERAL |
|   | 1030 | M.Powell | Bilateral Total Knee Arthroplasties | Edwards, Robert | 50 | SDSO | GENERAL |
| 7 | 730 | D.Reeves | Removal Internal Wires and Arch Bars | Schneider, Hannah | 39 | SDS | LOCAL |
|   | 830 | D.Reeves | Maxillary, Partial Mandibular O&A | Pruszynski, Cyril | 39 | SDS | LOCAL |
|   | 1000 | D.Reeves | Laser Vaporization Lesions Floor of Mouth and Tongue | Harrison, Suzanne | 72 | SDS | LOCAL |
| 8 | 730 | H.Patterson | Right Carpal Tunnel Release | Gere, Cynthia | 33 | SDS | LOCAL |
|   | 830 | H.Patterson | Left Carpal Tunnel Release | Thomas, Jack | 32 | SDS | Local |
| 9 | 930 | H.Patterson | Right Cubital Tunnel Release | Smith, Robert | 30 | SDS | GENERAL |

| | | | | | 3:55 PM | |
|---|---|---|---|---|---|---|
| File Patients Schedule Locations Reports | | | | | | |

Surgical ICU: Patient Status 09/23/1994

| Charge RN: | Caplan | CCM Attending: | Strum #2334 |
| Secretary: | Jones | CCM Senior Fellow: | Michaels |
| Resp.Therapist: | Pulmon | CCM Fellow: | Bargas |
| CN Manager: | Johnson | Anesthesia Resident: | McCoy |
| Pharmacy: | Haig | | |

| Bed# | Patient | Nurse | CCM Resident | Surgeon | Comments |
|---|---|---|---|---|---|
| 1 | Benson, Edward | Johnson | Bent | R.White | |
| 3 | Schneider, Hannah | Sneider | Wallace | D.Reeves | |
| 2 | Rohan, Gerald | Jones | Smith | C.Jergel | |
| 4 | Quinn, Melissa | Black | White | R.Reed | |

<<ADMISSIONS>>

| Requester | Priority | Location |
|---|---|---|

<<DISCHARGE>>

| Patient | Surgeon | Priority | Destination |
|---|---|---|---|

OR UTILIZATION
09/23/1994

| Budgeted | Scheduled | Used | Actual (%) | Accuracy (%) | Forecast (%) |
|---|---|---|---|---|---|
| OR 1: 8 | 1.75 | 3.33 | 42 | 52 | 22 |
| OR 2: 8 | 6.5 | 7.7 | 96 | 84 | 81 |
| OR 3: 8 | 3.25 | 4.83 | 60 | 67 | 41 |
| OR 4: 8 | 7.5 | 5.03 | 63 | 149 | 94 |
| OR 5: 8 | 5.5 | 4.42 | 55 | 124 | 69 |
| OR 6: 8 | 8 | 9.58 | 120 | 84 | 100 |
| OR 7: 8 | 4.0 | 2.35 | 29 | 170 | 50 |
| OR 8: 8 | 3.75 | 9.17 | 115 | 41 | 47 |
| OR 9: 8 | 3 | 7.78 | 97 | 38 | 38 |
| OR 10: 8 | 4.5 | 2.33 | 29 | 193 | 56 |
| OR 11: 8 | 8 | 5.95 | 74 | 134 | 100 |
| OR 12: 8 | 9.0 | 10.08 | 126 | 89 | 112 |
| OR 14: 8 | 4.25 | 4.5 | 56 | 94 | 53 |
| OR 15: 8 | 4.5 | 3.0 | 38 | 150 | 56 |
| END01: 8 | 0 | 0.0 | 0 | N/A | 0 |
| END02: 8 | 0.75 | 1.58 | 20 | 47 | 9 |
| CYS: 8 | 0 | 0.0 | 0 | N/A | 0 |
| HAAY: 8 | 0 | 0.0 | 0 | N/A | 0 |
| CL: 8 | 0 | 0.0 | 0 | N/A | 0 |
| Total: 152 | 74.25 | 81.65 | 53.7 | 90/9 | 48.8 |

© 1993, SIMS.

Graphical    CANCEL

| | | | OR UTILIZATION | | |
|---|---|---|---|---|---|
| | | | 09/23/1994 | Budgeted | |
| | | | | Scheduled | |
| | | | | Used | |

OR 1:
OR 2:
OR 3:
OR 4:

OR-12

| SCHEDULED | DURATION | NAME: | SURGEON: | PROCEDURE: |
|---|---|---|---|---|
| 730 | 3.5 | Benson, Edward | R.White | Right Total Hip Arthroplasty (Multilock) |
| 1100 | 5.5 | OMalley, Charles | R.White | Revision Left Total Hip Arthroplasty AML, Proximal Femoral A... |

OR 11:
OR 12:

OR-12

| ACTUAL | DURATION | NAME: | SURGEON: | PROCEDURE: |
|---|---|---|---|---|
| 855 | 4.17 | Benson, Edward | R.White | Right Total Hip Arthroplasty (Multilock) |
| 1335 | 5.92 | OMalley, Charles | R.White | Revision Left Total Hip Arthroplasty AML, Proximal Femoral A... |

CL:

ACTUAL: 53.7 % (Used/Budgeted)
ACCURACY: 90.9 % (Scheduled/Used)
FORECAST: 48.8 % (Scheduled/Budgeted)

Numeric          CANCEL

© 1993, SIMS.

| | | | | | | 3:58 PM |
|---|---|---|---|---|---|---|
| File | Patients | Schedule | Locations | Reports | | |

=== Transaction Register ===

Date: [09/23/1994] TO [09/23/1994]

Time: [0900] TO [2400]            Procedure: [    ]

Sort by: [Name ▼]  48              Location: ☒ ALL  ☐ SDS  ☐ HOLDING  ☐ ORs
                                              46      ☐ PACU ☐ ICU    ☐ SDS-2

| Patient | Location | Time In | Scheduled | Patient | Anesthesiologist |
|---|---|---|---|---|---|
| Benson, Edward | OR | 1602 | 730 | R.White | May |
| Benson, Edward | HOLDING | 1600 | 730 | R.White | May |
| Benson, Edward | SDS | 1600 | 730 | R.White | May |
| Gere, Cynthia | OR | 1602 | 730 | H.Patterson | Biers |
| Gere, Cynthia | HOLDING | 1601 | 730 | H.Patterson | Biers |
| Gere, Cynthia | SDS | 1600 | 730 | H.Patterson | Biers |
| Guest, Anna | OR | 1601 | 730 | H.Anderson | Gunnerson |
| Guest, Anna | SDS | 1600 | 730 | H.Anderson | Gunnerson |
| Haney, Reida | PACU | 1601 | 730 | R.White | Bargass |
| Haney, Reida | SDS | 1600 | 730 | R.White | Bargass |
| Louis, Lewis | ICU | 1601 | 730 | R.Novak | Johnson |
| Louis, Lewis | SDS | 1600 | 730 | R.Novak | Johnson |
| Quinn, Melissa | OR | 1601 | 730 | R.Reed | Watkins |
| Quinn, Melissa | SDS | 1600 | 730 | R.Reed | Watkins |

FIG. 10

COMPUTER-BASED SURGICAL SERVICES MANAGEMENT SYSTEM

This is a continuation of application Ser. No. 08/323,137 filed on Oct. 14, 1994 now abandoned.

BACKGROUND OF THE INVENTION

1. Field of the Invention

The present invention relates to a computer-based surgical services management system designed to address communication, utilization review, quality assurance, and resource coordination needs of a modern medical center.

2. Description of the Related Art

Today, medical centers are subject to severe financial, social, academic, political, and organizational pressures resulting from increased demands on services and limitations in health care resources. Modern academic medical centers must help address these difficult problems in resource allocation and utilization. Analysis performed on health care figures in 1981 estimates that surgical patients in acute care hospitals cost almost 25 percent of the United States' health care budget. Conservatively extrapolating to more current data, it is estimated that surgical services expenditures in the United States will reach $170 billion in the very near future. Inefficiency in the process of patient care involving surgical services could be extremely costly to individual hospitals and the nation. Likewise, the potential savings for hospitals that can operate more efficiently is enormous. A modest one percent increase in efficiency provides potential savings in the nation's health care budget in one year which could approach $1.7 billion.

A modern medical center poses cultural and technical problems in surgical services management. Surgical services in a typical medical center comprise the following units: an inpatient ward, a same day (outpatient) surgery (SDS) unit; preoperative patient holding areas; operating room (OR) suites; anesthesia, surgery, and nursing personnel; a postoperative or postanesthesia care unit (PACU); a surgical intensive care unit (ICU); laboratories; and radiology, pathology, respiratory care, and support services.

Surgical services represent a complex, resource-intensive operation. Because of this complexity, significant inefficiency has long been accepted by most medical center managers. Unlike industrial manufacturing, the medical industrial complex has been relatively immune from rigorous analysis. The origins of such immunity are historical, cultural, and financial. Recent changes in the health care enterprise compel a systematic approach to coordinated delivery of surgical services and patient care.

A distributed communication, resource coordination, and utilization system can have a significant, positive impact on the utilization of critical, costly resources involved in the care of surgical patients. Most medical centers operate surgical services (excluding emergency patient care) at an estimated 50 to 60 percent utilization. With a real-time resource coordination system, operating rooms could be at least 80 percent utilized in the care of elective surgical patients.

Medical and industrial management literature emphasizes the need for operational effectiveness in surgical services, but does not offer the solutions provided by the present invention. Reviewed below are various health care sectors' approaches to increased efficiency in surgical services.

Surgical services are expensive, and the need to operate efficiently and effectively is recognized internationally. The OTIS system, developed at the Aberdeen Royal Infirmary, allows operating room staff to enter data using microcomputers and to review the durations of various procedure to predict future operating room utilization. Their goals were to direct the schedule of surgery so that each surgical session would regularly finish on time, which saves costly personnel time. Operating room utilization is reviewed using bar graph displays. Utilization review can be keyed to specific surgeons, a design feature requested by the surgeons.

Assembling a project team for designing a successful operating room scheduling system is a major undertaking. An article by M. Choy entitled "Implementing a Computerized Operating Room Management System", *Journal of the Society for Health Systems*, Vol. 2, pp. 103–19 (1990), describes the process by which a team was formed to implement such a system at The Queen's Medical Center in Honolulu. Their system focuses on materials management more than on scheduling. It supports the timely availability of materials used in the operating room rather than on the impact of operating room scheduling decisions on upstream or downstream hospital facilities.

To support prospective and reactive scheduling, it is necessary to gather utilization data to establish trends in surgical services demand. W. M. Hancock et al., in "Operating Room Scheduling Data Base Analysis for Scheduling", *Med. Svs.*, Vol. 12, pp. 397–409 (1988), proposed an algorithm for determining how to extract statistically distinct subsets from a surgical database, to more accurately estimate the variance of surgical procedure times. Both variances and mean times are necessary to determine realistic starting times for cases which follow starting cases. These investigators also discuss issues related to periodic updating of the database.

W. M. Hancock and M. W. Isken, as reported in "Patient-Scheduling Methodologies, *Health Sys.*, Vol. 3, pp. 83–94 (1992), surveyed a custom admissions scheduling system, ASCS, which controls inpatient admissions and coordinates those admissions with surgical scheduling. The result is a higher hospital occupancy rate without an increase in staff anxiety levels. Their system considers both operating room scheduling within the larger context in which it functions and overall efficiency measures, rather than just operating room utilization, as an indicator of system value. ASCS appears to be used in centralized planning and to be based on a hospital simulation model. The investigators define a set of elements comprising a state-of-the-art operating room scheduling system, one of which is a networking capability, but the ASCS does not incorporate this feature. Although Hancock and Isken recognized the difference between inpatient and outpatient admissions, their program did not incorporate this distinction, nor did it allow for reactive planning of emergency surgery.

The operating room management system at Johns Hopkins described by E. E. McColligan et al. in "Automated Utilization Analysis As A Foundation for Effective Operating Room Management", *Eighth Annual Symposium on Computer Applications in Medical Care (SCAMC)*, Washington, D.C, pp. 227–30 (November 1984), supports block scheduling, utilization review analysis, and centralized decision-making. This system is written in MUMPS, and runs on a mainframe computer, but it does not appear to perform real-time or reactive adjustment to schedule disruptions, nor does it consider hospital facilities outside the operating room. It is a valuable and effective tool for predictive scheduling, utilization review, and resource planning (see the article by McColligan et al. for a system description and an article by T. Gordon et al., "Surgical Unit Time Utilization Review: Resource Utilization and Management Implications," *Med. Sys.*, Vol. 12, (3), pp. 169–79 (1988), for the system's utilization review, data collection, and interpretation function), but its architecture and implementation platform are not designed for distributed, real-time replanning and communication of adjustments.

SUMMARY OF THE INVENTION

The present invention overcomes the deficiencies and problems of the prior art noted above by providing a computer-based surgical services management system which addresses the communication, utilization review, quality improvement, and resource coordination needs of a modern medical center. The present invention addresses the following areas:

Dissemination of site-specific information related to the work process in other units of surgical services, so that decisions are based on accurate, instantaneous appreciation of the overall situation. This improves reactive coordination of personnel, space, and equipment.

Providing an unobtrusive, reliable, and accurate method to record surgical services utilization data for analysis and subsequent predictive scheduling of hospital resources, including personnel, space, and equipment.

Improving the quality and accuracy of data by automating its collection.

Empowering health care providers, by returning locally generated data to those who collect and use it.

Improve time management and operational efficiency of key health care professionals and administrators involved in the delivery of surgical services.

Document surgical diagnoses and procedures perioperatively as an objective basis for total quality improvement.

Explore the technical and cultural problems inherent in improving communications among health care professionals and the process of cultural change including how information management systems function in the health care environment.

The present invention provides a rational, data-driven method for resource allocation and management in surgical services that focuses primarily on optimizing communications and coordination of surgical resources. Research indicates that of the three major clinical components comprising the health care system (surgical, medical, and mental health), surgical services is the most amenable to cost control by a systematic process of utilization review.

Accordingly, the present invention is a computer-based surgical services management system for communicating between site locations of a surgical services facility. The system includes a computer workstation located at each site location of the surgical services facility. A server is connected in network communication with each workstation, and a database resides on the network, as described below.

The database retains patient-specific data maintained temporarily by the workstation located at a site where a patient is located. The patient-specific data moves from site to site with the patient. Site-specific data on the database is maintained at the site where the site-specific data is produced.

The database is distributed to and contained within each workstation for editing by a user. A copy of the database contained in each workstation is duplicated by the server. Preferably, each workstation has a local hard disk memory device.

Preferably, the database is of an object-oriented design. The object-oriented database contains classes for patients, locations, resources, surgeons and anesthesiologists. Methods are assigned to each of the classes for updating information. Methods also are assigned to perform constraint propagation in the network to maintain data structure.

The database also contains a plurality of modules for maintaining and displaying the patient-specific and site-specific data. The modules include a system status module, a scheduling manager, a calendar, a report writer, and a data archive and analyzer. For ease of use, the system preferably includes a graphical interface for accessing the modules.

The system network can be maintained by a server which can be a single workstation, or any number of workstations. Workstations can be located in various locations involved in providing surgical services, including patient homes, same-day surgery facilities, holding areas, operating rooms, postanesthesia care units, intensive care units, and hospital ward floors. The server is in network communication with each workstation using a network which is preferably a 10 Base T ethernet using either TCP/IP or Ethertalk protocols.

The network further includes repeaters for reading data from the distributed database and presenting the data to the user. User input and editing capabilities are not provided on these repeaters. For remote communications, the network further includes a modem for remote access to the database. The system preferably includes security access controls and password protection for ensuring patient and hospital privacy.

In addition, the database further includes personnel data for maintaining information regarding personnel. Typically, the personnel include surgeons, anesthesiologists, and nurses. Also, the database includes equipment data for maintaining information regarding equipment used in relation to surgical services. The information in the database is preferably written to a text file, for example an ASCII or other DOS-based file, to generate a transaction register.

The system preferably uses bar codes to input information representing data specific to each patient. Time-of-day information is also available, and a computer-based application combines the bar code information and time-of-day information to track and record residence and procedure times so that an audit trail is produced relative to a time course and geographic progression of patients through surgical services. A transaction receipt is produced representing a written record of surgical services provided and who provided them. Further reporting capabilities include utilization screens and time categories. Time categories, according to the present invention, include available time, scheduled time, actual time. These are combined to produce actual utilization= actual time/available time, efficiency of utilization= scheduled time/actual time, and forecast utilization= scheduled time/available time.

The invention also includes a computer-implemented method of managing data and communicating between site locations of a surgical services facility. The method includes the steps of establishing a computer database which has patient-specific data, site-specific data and an interface for user access of the data and distributing the database on a peer-to-peer computer network. The peer-to-peer network includes individual workstations, with selected workstations being located at each of the various site locations. A copy of the database is contained on each of the individual workstations, and a copy of the database contained on each of the individual workstations is contained in a network server. The workstations on the computer network are used to maintain and display information in the database. Changes to the information of the database which are made on each of the workstations are duplicated on the server. Changes are updated to each of the other workstations on a periodic basis.

Other features and advantages of the present invention will become apparent from the following description of the invention which refers to the accompanying drawings.

BRIEF DESCRIPTION OF THE DRAWINGS

FIG. 3 is an operating room schedule in its classic configuration.

FIG. 4 is an illustration of the operating room schedule reconfigured as a Gantt chart for reactive scheduling.

FIG. 5 is an illustration of the real-time throughput tracking Gantt chart illustrating scheduled (open bar) and used (filled bar) operating room residence times.

FIG. 6 is an information screen for the surgical intensive care unit.

FIG. 8 is a numerical utilization review screen (the numerical counterpart of FIG. 7) consisting of a matrix displaying three categories of time (budgeted, scheduled, used) and three summary utilization statistics (actual, accuracy, and forecast) for each operating theater.

FIG. 9 is a graphic utilization review screen pop-out feature giving access to details of case duration and starting times both scheduled and used.

FIG. 10 is a transaction register with selection and sort buttons for extracting data on-line.

DETAILED DESCRIPTION OF THE PREFERRED EMBODIMENT

Before describing the architecture and operation of the system of the present invention, a brief description of the pattern of patient care in connection with the rendering of surgical services is appropriate.

I. Patterns of Care in Surgical Services

To allocate a specific starting time and duration for surgery, a surgeon's office typically contacts the admitting office and requests a reservation with an allotted time block. Requests are recorded in the admitting office and, together with information on surgical teams and operating room availability, are used to generate a prospective surgical schedule. The preliminary schedule is published and subsequently modified by nursing and anesthesia departments according to pragmatic needs associated with availability of laboratory testing, personnel, space, materials, and patients. Patients are informed of their scheduled date of admission, and preoperative consultation and laboratory studies are arranged. When the patient is admitted, information stored in the admitting office is transferred, in writing, to the various site locations in which the patient receives services and combined with new information generated in each location. Without a computer-based communication system, as the patient moves through surgical services, information must be laboriously rewritten at each new geographical location.

Figure 1:
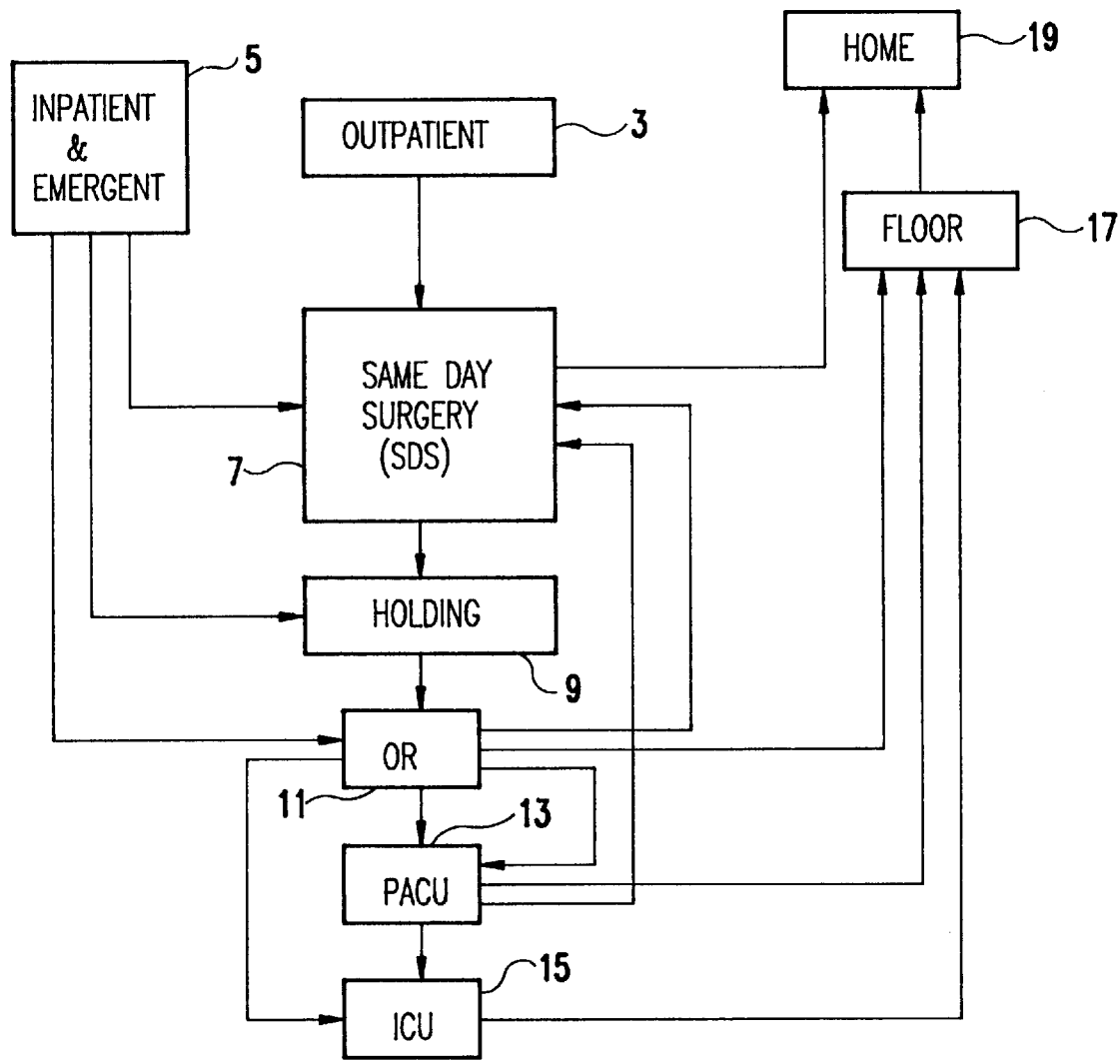
FIG. 1 is a schematic plan of the traffic flow and specific geographic locations through which patients traverse while receiving surgical services.

The major geographic locations through which patients traverse while receiving surgical services are illustrated in FIG. 1. Efficient throughput depends on efficient movement from location to location. Most patients arrive as outpatients 3 or inpatients 5 early on the day of surgery, accompanied by their families. A medical and nursing history is obtained, laboratory data are checked, and the patients are dressed for the operating theater. When ready, the patients are sent to holding area 9 near operating theaters 11, where they are interviewed by an anesthesiologist. The consent for surgery is obtained by a member of the surgical team. Inpatients come directly to holding area 9 from the inpatient wards 5. In holding area 9, patients often request to speak with their family or surgeons before entering surgery. Intravenous infusions are initiated, shave preps are performed, and occasionally casts are removed. If indicated, regional anesthesia can be begun using special equipment and monitoring.

When anesthesia, nursing, and surgery personnel are ready, the patient is transported to the scheduled operating theater 11, transferred to an operating table, monitored, and anesthetized. Surgery begins 30 to 60 minutes after the patient enters the operating room. After surgery, the patient is transported to PACU 13 where he/she recovers for up to 60 minutes before being transferred to a ward bed on floor 17 or to SDS unit 7. Patients who are moved to a ward on floor 17 stay until their recovery can be managed at home 19. Patients who return to SDS 7 are reunited with their families, ambulated, instructed on follow-up care, and discharged home 19.

A small number of patients are sufficiently ill to require admission to ICU 15 after surgery. The surgery and anesthesia teams make the admission decisions together and are responsible for arranging reservations and admissions. ICU's 15 are remote from operating suite 11, and communications are by phone. Anesthesia providers must notify control personnel at ICU 15 and arrange for beds, equipment, and medical personnel before the move. In some instances, the patient is taken to postanesthesia care unit 13 and later moved to ICU 15.

Many problems affect a smooth progression of patients through the surgical services suites. These include, but are not limited to, late arrivals of patients or medical records, delays in support services, acute onset of abnormal medical conditions (infections, chest pain, and the like) requiring delay or cancellation of procedures, inaccurate or inappropriate reservations, lack of a mechanism to enable dynamic scheduling, and delays that result in lost professional time. Poor use of time results from these and other problems, leading to peaks and troughs in the demand for surgical services and adding to inefficiency and dissatisfaction among patients, their families, and health care providers.

II. Overall Architecture of the System

Figure 2:
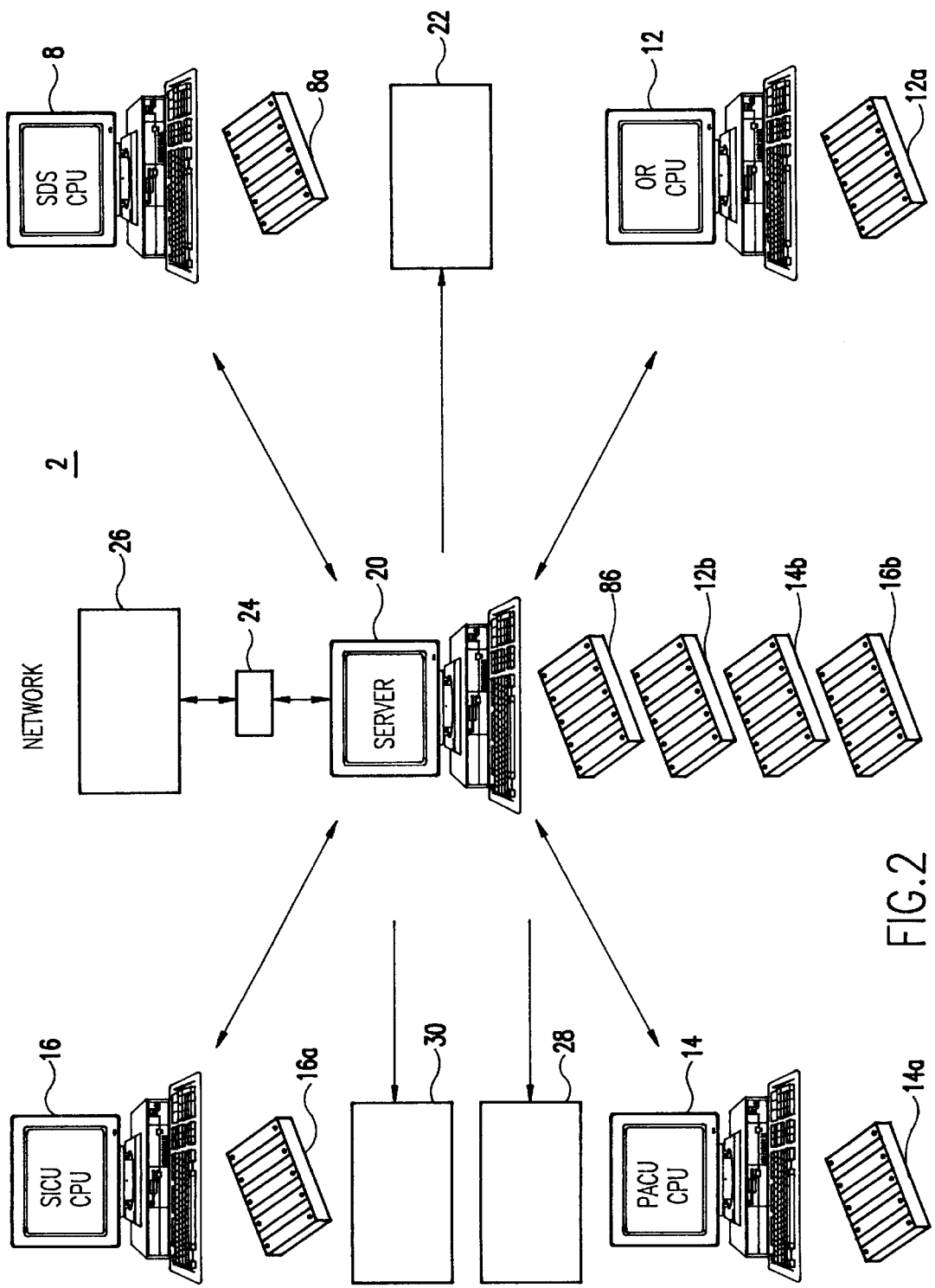
FIG. 2 is a network schematic illustrating the distributed database and coordinating server.

In the preferred embodiment of the present invention, each site through which patients traverse while receiving surgical services is a node on a local area network. Such a local area network 2 is represented in FIG. 2. A workstation is located at each node, such as SDS central processing unit (CPU) 8 located in SDS 7, OR CPU 12 located in OR 11, PACU CPU 14 located in PACU 13, and SICU CPU 16 located in SICU 15.

According to the preferred embodiment of the present invention, a copy of the database resides on each workstation located at each particular site. Thus, SDS CPU 8 has resident thereon a copy 8a of the database application. Medical personnel at each site location are thus able to view and edit data in the copy of the database resident within that site's CPU.

Various security permissions and access capabilities can be prescribed by system design and control. Generally, however, it is preferred that within surgical services sites, nominally restricted access be provided in the interest of maximum information access and patient care. Outside the surgical services area, access is preferably more restricted with regard to patient and hospital confidentiality.

Thus, in the preferred embodiment of the present invention, view privileges are unrestricted throughout the system in the cause of disseminating information. Under specific circumstances (for example, the family waiting area), view permissions can be restricted or denied by use of passwords and permissions jointly agreed upon by the users and system administrator.

As the patient progresses through the surgical services flow, patient-specific data can be edited at each site while the patient remains at that location. Accordingly, while the patient is in OR 11, patient data can be viewed and edited at workstation OR CPU 12. A record is kept of changes to the data, including a time-stamp based on a network system clock and location and/or personnel information being attached to changes made, when necessary. Accordingly, an audit trail of the time of each change, and the personnel and location responsible, can be generated. Although some patients can follow nonstandard paths through the surgical facility, most follow the patterns illustrated in FIG. 1.

III. Database Description

FIG. 2 show network 2 in schematic form and illustrates the workstation sites described above in communication with a coordinating server 20. In the preferred embodiment of the present invention, the database is distributed to each workstation on the network 2. The network is designed to communicate with independent workstations, all reading from common coordinating server 20 designated for the exchange of information. Database copies 8a, 12a, 14a, and 16a are distributed to respective locations, where it is stored, with locally owned data (i,e., data edited at that location), on a local hard disk. Additionally, data is written to coordinating network server 20, which mirrors the distributed database (FIG. 2) to maintain corresponding server copies 8b, 12b, 14b, and 16b. Although FIG. 2 represents server 20 as a single workstation, alternatively several workstations could function as servers or as back-up servers in the event of a server malfunction.

Periodic, system-wide updates are used to provide current information to all nodes on the network and to maintain system integrity. Update frequency can be determined based on system and facility demands. In a preferred embodiment of the present invention, system-wide updates take place approximately every five minutes.

As a result of the distributed, peer-to-peer network design according to the preferred embodiment of the present invention, data is not lost in the event of a workstation malfunction at a particular site. Only editing capabilities are lost at the affected site. A copy of the database continues to be available to other locations on the network. Reciprocally, in the event of a server malfunction, the copy of the database continues to be present on the site location workstation. Through designation of a back-up server, information and communication ability is always maintained.

In a particularly preferred embodiment of the present invention, the peer-to-peer network functions on an industry-standard backbone, consisting, for example, of a 10 Base T ethernet using either TCP/IP or Ethertalk protocols.

IV. Database Structure

The database contains two categories of data: patient-specific data (owned temporarily at the site where the patient is located) and site-specific data (owned at the site where the data is produced). As described above, ownership of and responsibility for patient-specific data moves electronically through the network 2 as the patient moves from location to location (FIG. 1).

Site-specific data, on the other hand, are entered and maintained locally, and electronic ownership of these data remains there after the patient has moved to new locations. In all cases, edit privileges for data follow the electronic ownership, but, if indicated administratively, can be assigned to specific distant sites or users.

Figure 12:
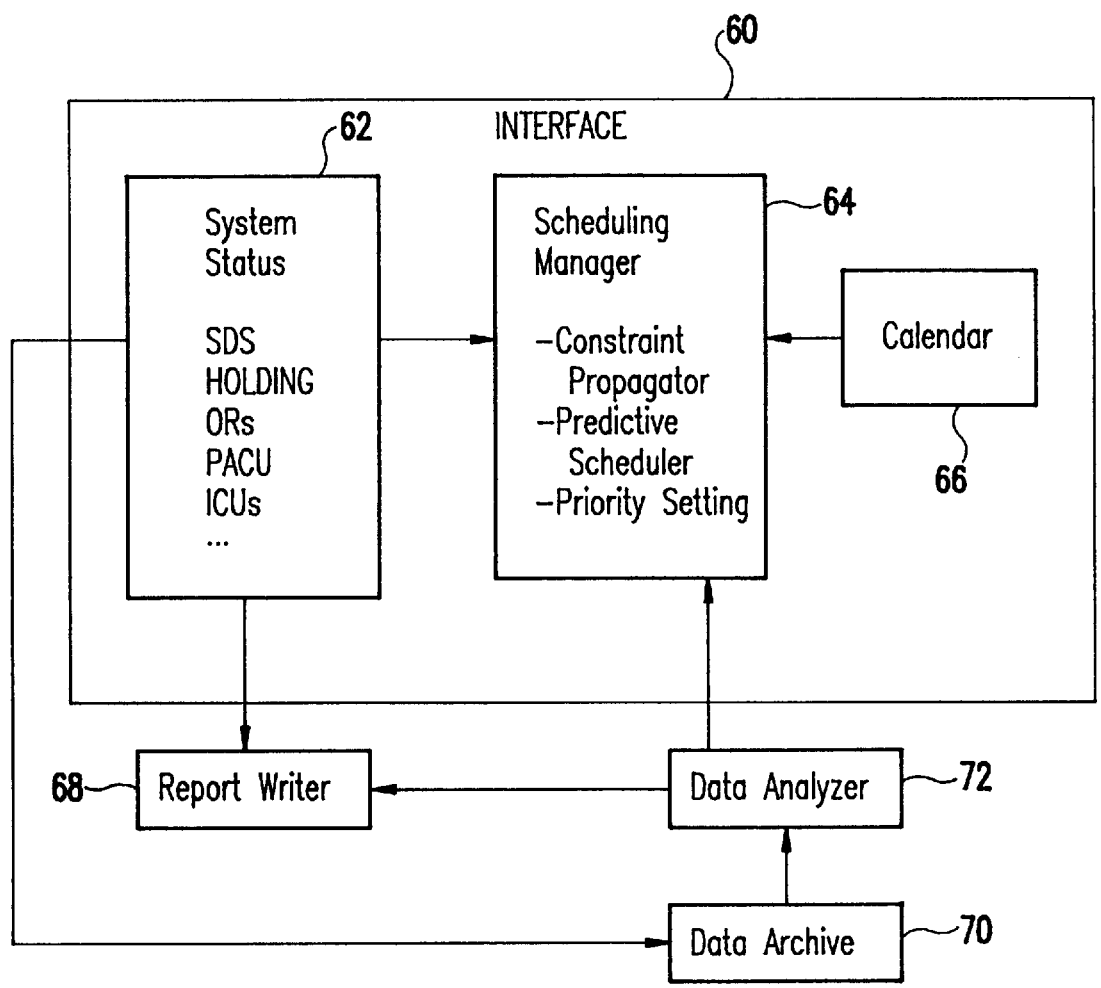
FIG. 12 is the architecture of an embodiment of the present invention, consisting of five modules.

All components of the system within the interface box in FIG. 12, and the interface itself, are written in an object-oriented language (i.e., LISP, Smalltalk, C++etc.). See D. A. Taylor, Ph.D., "Object-Oriented Technology: A Manager's Guide", Addison-Wesley (9th ed., 1994), which provides an introduction to object-oriented design and programming, incorporated herein by reference.

To enable rapid exploration of concepts, a prototype was implemented in LISP. Patients, personnel, and resources are instances of a hierarchy of frames, or classes. There are four primary classes in the hierarchy:

patients
 personnel—surgeons, anesthesiologists, CRNAs, nurses, and residents
 rooms—ORs, surgical intensive care unit beds, postanesthesia care unit beds
 equipment A. Object-Oriented Programming Object-oriented LISP allows for user-centered design and rapid prototyping. It also permits the adoption of a continuous improvement philosophy in software development that insures that the software continues to change with evolutions in health care. This concept, called maneuverability, is the ability of a software system to adapt flexibly to the changing demands of users and the marketplace. Modularity also improves maintainability and allows addition and subtraction of modules without interfering with existing software cohesiveness.

The use of objects allows rapid prototyping and implementation of a calendar from which daily schedules flow. Because objects are used, it is possible to have two separate daily schedules coexist. Such a feature is useful for performing predictive scheduling.

Object-oriented representation of both patients and resources also simplifies the data collection procedure. The patient object, an instance of the patient frame shown in the example below, includes slots that record the expected path of the patient through surgical services, the scheduled times for significant events along that path, the expected service time for each stop along the path, the path of the patient through surgical services, the used times for significant events along that path, and the used service times for each stop along the path. As each patient completes his/her course through the system, the present invention records both the planned and used service record, along with patient demographics (age, and so forth), the procedure performed on the patient, and the major health care providers who cared for the patient.

---

EXAMPLE

```
(define-frame PATIENT
; scheduling/reservationinformation
    (last-name)
    (first-name)
    (age)
    (id-no)
    (physician)
    (attending-md)
    (procedure)
    (comments)
    (status)
    (requested-starting-time)
    (person-making-reservation)
    (pager-of-person-making-reservation)
    (scheduler-name)
    (anesthesia-type)
    (previous-location)
    (location :when-modified (daemon-update arrival-time))
    (next-location)
    (urgency-of-surgery :constraints(:one-of (emergent urgent elective)))
; sds information
    (sds-in-time)
    (time-sec-called)
    (time-rdy-or)
    (time-escort-called)
    (time-to-or)
    (time-expec-pacu)
    (nurse-assigned)
    (arrangements)
    (sds-room-to-go)
    (sds-ready-status :constraints (:one-of ("ready""not ready")) :default-values ("not ready"))
; initial caregiver's report
    (lines)
    (respiratory-set-up)
; procedure
    (blood-type)
    (iv-infusion)
    (height)
    (weight)
; 5th floor holding room information
    (id-confirmed :constraints (:one of ("yes""yes""no""no")))
    (level of consciousness :constraints (:one-of ("awake""drowsy""confused""awake""drowsy" "confused")))
    (consent-completed :constraints (:one-of "yes""yes""no""no")))
    (site-confirmed :constraints (:one-of ("yes""yes""no""no")))
    (h-and-p-on-chart :constraints (:one-of ("yes""yes""no""no")))
    (xray-lab-complete :constraints (:one-of ("yes""yes""no""no")))
    (shave-prep :constraints (:one-of ("yes""yes""no""no""na""na")))
    (op-initial)
    (pulse-initial)
    (ready-status :constraints (:one-of ("ready""not ready")) :default-values ("not ready"))
; pacu information
    (room-no)
    (ps)
    (pc)
    (pacu-in-time)
    (pacu-out-time)
; or scheduling information
    (scheduled-or-number :when-modified (daemon-anesthesiologist-assigner))
    (or-number)
    (event)
    (comments-or
; sicu room number
    (icu-room-number)
; sicu info
    (reservation-sicu :constraints(:one-of ("yes""no""yes""no")) :default-values ("no"))
    (sicu-bed :constraints(:one-of ("yes""no""yes""no") :default-values ("no"))
    (comments-admit-sicu)
    (comments-discharge-sicu)
    (comments-sicu)
    (priority-admit-sicu)
```

| EXAMPLE |
| --- |
| (priority-discharge-sicu)<br>(nurse-sicu)<br>(ccm-resident-sicu)<br>; time<br>   (arrival-date)<br>   (arrival-time)<br>   (admissions-arrival-time)<br>   (sds-arrival-time)<br>   (holding-arrival-time)<br>   (or-arrival-time)<br>   (pacu-arrival-time)<br>   (sicu-arrival-time)<br>   (holding-departure-time)<br>   (or-departure-time)<br>   (pacu-departure-time)<br>   (sicu-departure-time)<br>   (departure-time)<br>   (list-of-locations :multivalued t)<br>; personnel<br>   (surgeon)<br>   (anesthesiologist)<br>   (anesthetist)<br>; maintenance slots<br>   (list-of-patients)) |

B. Data Structures

In the preferred embodiment of the present invention, the following classes are defined:

Location__Class

Patient__Class

Resource__Class

Surgeon__Class

Anesthesiologist__Class

Each patient is an instance of the patient__class. All information about a patient is contained in a patient__instance. As the patient moves from location to location, a time stamp and the appropriate information related to the care of the patient is saved in appropriate slots of the patient__instance.

Hospital locations are instances of the location__class. They keep track of all the patients that are scheduled to go through them, that are currently in that location and that have passed through that location. They also keep records of all the personnel involved during the period of operation.

Surgeons are instances of the surgeon__class. The surgeon instances keep records of the patients on whom the surgeon will perform surgery, and the block times the surgeon has reserved for surgery. A surgeon may have several patients. Surgeons are also kept as part of the patient record.

On the other hand, anesthesiologists are instances of the anesthesiologist__class, and they are preferably assigned to operating rooms, that is, to location__instances, rather than to specific patients, although this optionally could also be the case.

As patients move from location to location, different staff is assigned to perform tasks on them. In the preferred embodiment of the present invention, methods are assigned to the patient__class to keep track of this personnel, and vice versa, the resource__instance keeps as part of its record a list of patients to which the resource is assigned.

Figure 14:
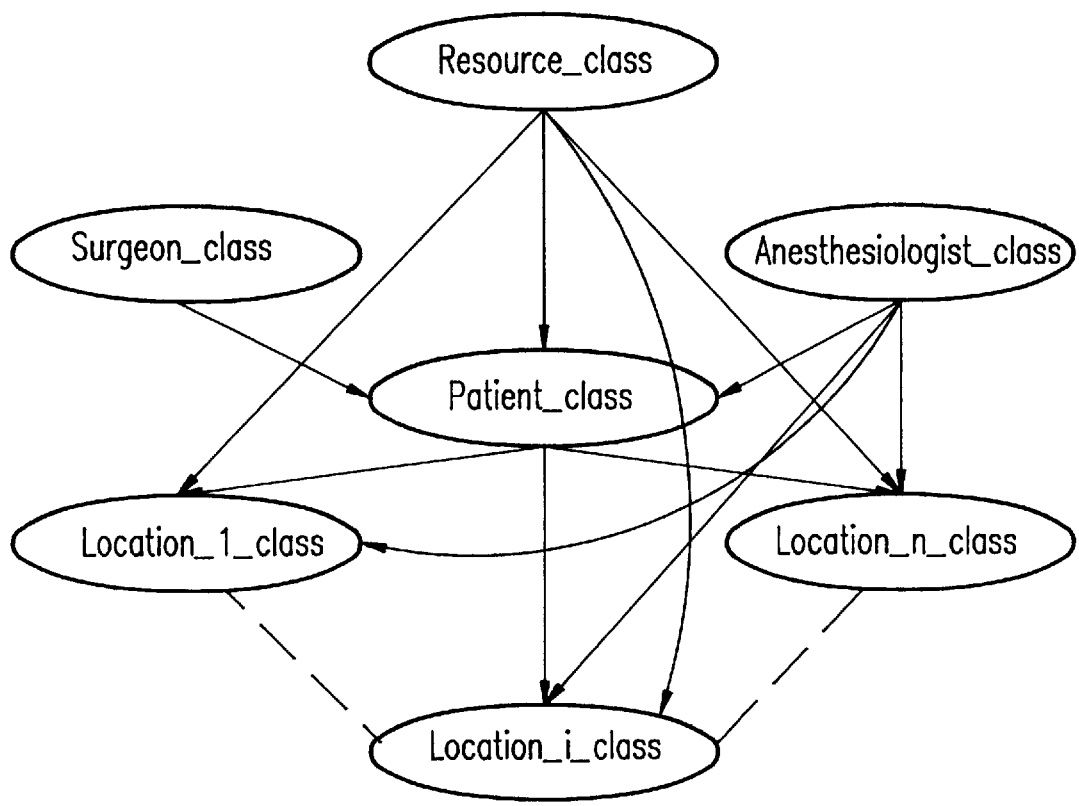
FIG. 14 is the relationships among objects illustrated as a data network as used in an embodiment of the present invention.
Figure 15:
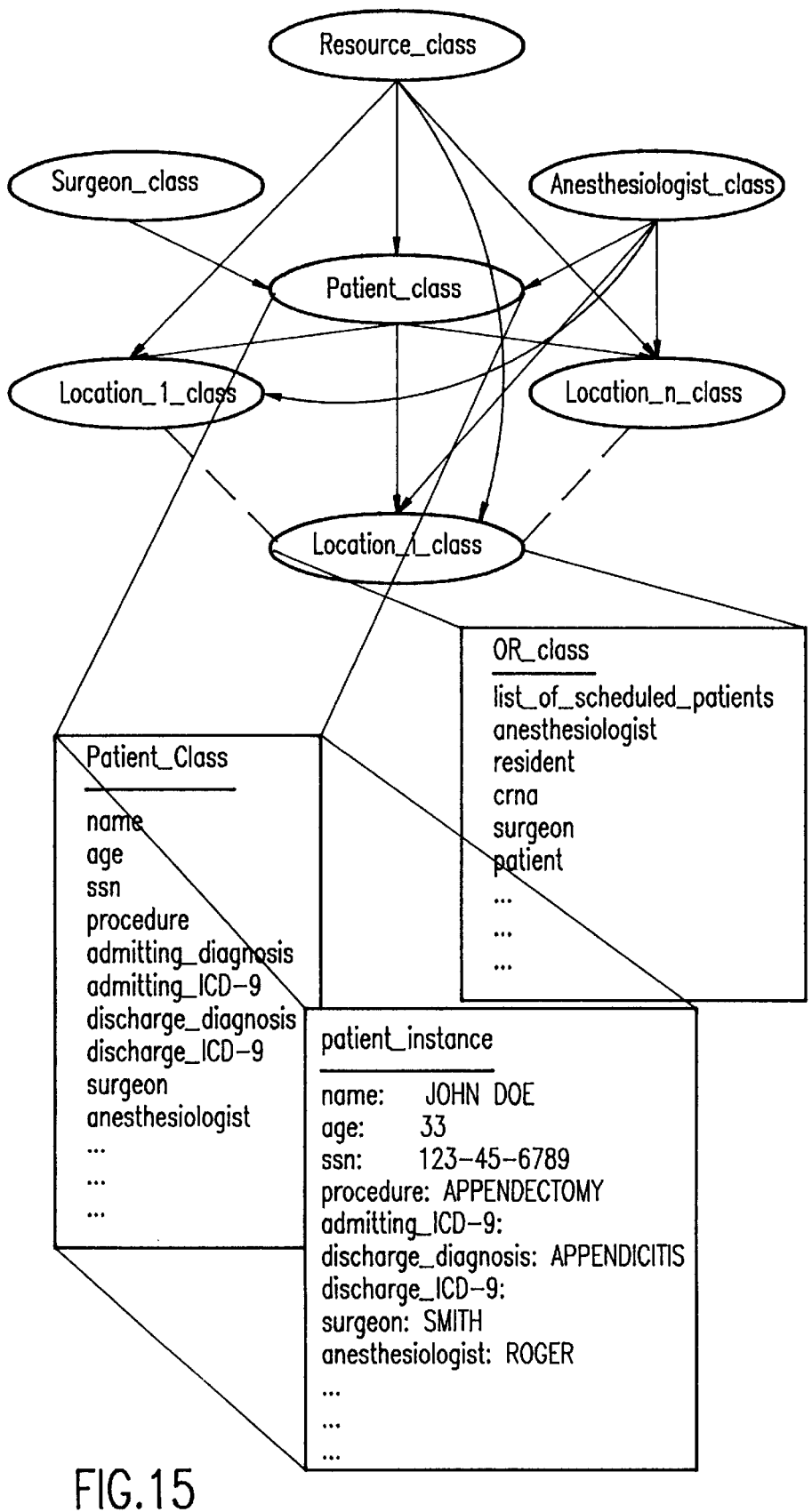
FIG. 15 is the relationships of FIG. 14 including certain classes and instances as used in an embodiment of the present invention.

Methods are assigned to classes to update the information of the defined instances (see FIG. 15) as they are changed as a natural consequence of the patient's progression through various geographic locations. Methods perform constraint propagation in the data network (FIG. 14) to maintain the data structures.

| Functionality Chart | |
| --- | --- |
| File | |
|    Load | (loads a file) |
|    Save | (saves a file) |
|    Network Setup | (selects servers) |
|    Quit | |
| Patients | |
|    Where is . . . ? | (locates a patient) |
|    Who is . . . ? | (lists patients in a location) |
|    Location 1 -   Move | (Move a patient) |
|                   Update | (Manual update - patient info) |
|                   Demographics | (display of patient data) |
|    Location i | |
|    Location n | |
|       Throughput Data | |
|          Individual Patient (audit trail of a patient) | |
|          All Patients (graphic display: status all patients) | |
|       OR Utilization | |
|          Today (Default) | (ratio - used:budgeted OR time) |
|          Last Week | (Cumulative OR utilization) |
|          Last Month | |
|    Utilities | |
|       Sign in | (Patient sign in on arrival) |
|       Admit | (Admit the patient) |
|    Reservations | |
|       Select Month/Day | (calendar for reservations) |
|       New Patient | (Create a new patient object) |
|       Edit Patient Data | (Edit existing patient object) |
|       Delete Patent | (Delete a patient object) |
|       Gantt chart | (Graphic display of OR schedule) |
| Locations | |
|    Surgical Service Desk (Nursing preparation for surgery) | |
|    Holding Room    (Anesthesia preparation for surgery) | |
|    OR -   OR Board  (Current status of each OR) | |
|          OR Staff    (Staff assigned to each OR) | |
|    PACU | (Post Anesthesia Care Unit) |
|    ICU Board | (Intensive Care Unit) |
| Reports | |
|    Transaction Register (All transactions in surgical services) | |
|    Patient Transmission Record   (A patient receipt listing the duration of surgical services, diagnosis and key personnel) | |

C. Functionality Transparent to the User

When a patient object is created, it is assigned to a file corresponding to a date selected in a calendar.

When a patient is assigned to an operating room, he/she inherits information from the operating room such as staffing information, special equipment and so on.

When the patient arrives at the hospital and signs in, a time stamp is generated. As the patient moves from location to location, new time stamps are created to provide an audit trail of the path traversed and the duration in each geographic location.

Each location generates data which is stored in the patient instances. In addition, each location stores in its own instance time stamped data related to the resources used.

Objects at each location are automatically updated at intervals from the server(s).

V. Specific Features of the System

The system of the present invention includes a number of unique features, which will now be described.

A. Repeaters

Several computers in the network do not possess data ownership. They are repeaters 22 (FIG. 2), which read data from the distributed database and then presenting it to the user. These workstations are not passive, because each must actively configure the data to site and user-specific criteria governed by the user-interface design before presenting it to the user. Repeaters are placed in areas where providers must access the distributed database but where patients are not housed. Such locations include the surgical and staff lounges, locker rooms, anesthesia offices, equipment rooms, central supplies, pharmacy, emergency department, and so forth.

B. Remote Access

Remote access via modem-based repeaters 26 is provided via modems 24 so that properly authorized users from remote locations, such as doctors' offices, nearby hospitals, and so on can check the availability of surgical devices, operating suites, and the progress of surgery in real time.

C. Data Archive

Time-stamped data is compressed and written to an archiver 28 that maintains historical records. The archiver runs in tandem with a duplicate 30 to prevent data loss.

D. Reactive Scheduling

FIG. 3 is a computer screen image showing an operating room schedule 32 in its classic configuration before the present invention. Although it contains all the information necessary to administer a surgical services facility, it does not convey scheduled interactions with respect to time and space.

Figure 4:
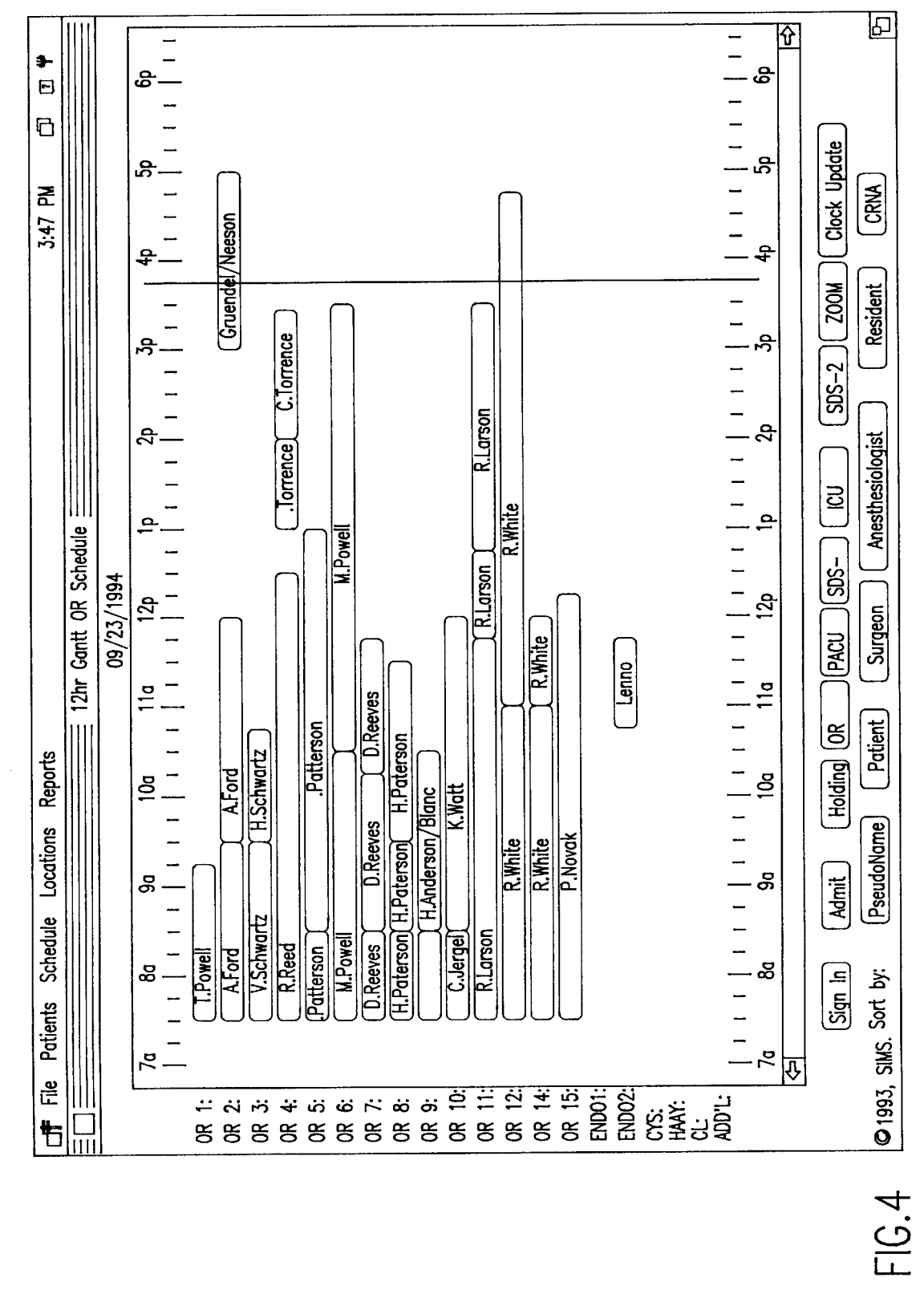

To better view and manipulate the schedule, it can be reconfigured in a single-day Gantt chart display. The Gantt chart (FIG. 4) illustrates the progress of surgery and rebroadcasts changes in the surgical status in real time. According to the present invention, on-line data access allows health care providers themselves to become self-directed, helping to improve coordination and more efficient utilization of materials and personnel. Contrasting designs and colors, for example, can be used to highlight information in the display.

E. Predictive Scheduling

Predictive scheduling is facilitated using a multi-month calendar display. Entire operating room schedules can be compiled days to weeks in advance. Each daily schedule is available as a Gantt chart. Broad access to these Gantt charts improves utilization of time, personnel, and materials by allowing operating room personnel and surgeons to examine future demands and to plan use of the operating room resources.

F. Scheduling

Utilization review statistics are available for the study of statistical process control, leading to improved predictive scheduling of the operating room and more efficient use of institutional facilities and operating time. The improved access to scheduling information allows many surgeons more direct access to operating room time. Improved reactive scheduling of the operating rooms allows more timely access to facilities for surgeons and patients. As the amount of available data increases, research will extend advanced operating room scheduling to improve access, business efficiency, and more predictable utilization of resources.

G. Throughput Analysis

Figure 5:
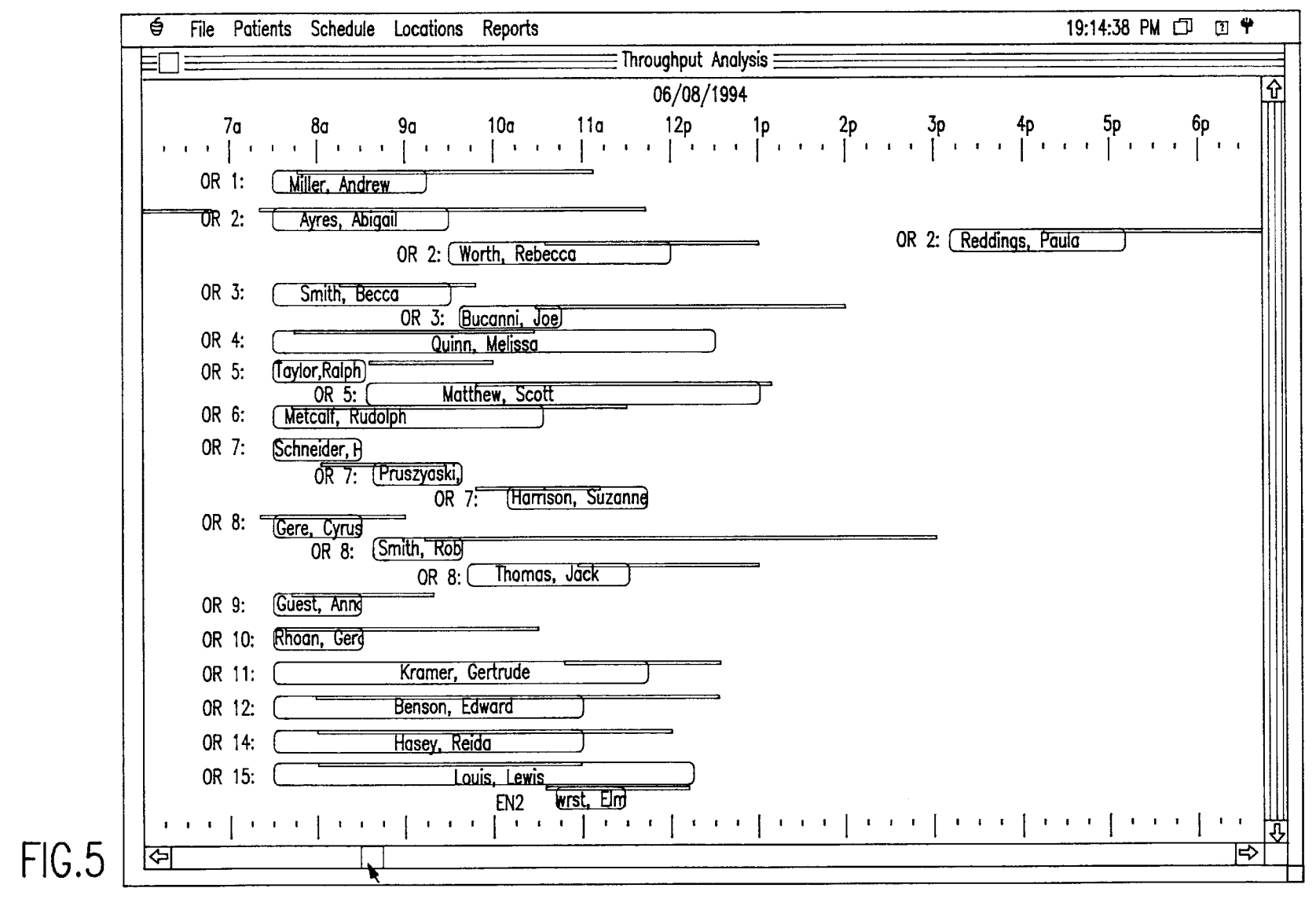

FIG. 5 is an illustration of the real-time throughput tracking Gantt chart illustrating scheduled (open bar) and used (filled bar) operating room residence times.

As patients move within the hospital, ownership of patient-specific data travels electronically with the patients from location to location. Time stamps are entered into the database by bar code (see FIG. 13) or direct keyboard entry as patients change locations, so that the length of stay in each location is documented. The time stamps are attached to the patient audit trail and are available for utilization review. Patient-specific audit trails are available on-line for each patient. Audit trails are summarized for all patients by the real-time throughput-tracking Gantt chart (FIG. 5). Analysis of the time spent in each location leads to a statistical description of the distribution of waiting periods and duration of procedures. By examining statistical trends and outliers, problem areas can be identified, and opportunities for improvement can be discovered.

H. Trend Analysis

Statistical summary of time intervals selected by procedure, provider, location, patient, or other characteristics can indicate trends over time, which can be used to prospectively manage resources, according to experience in preceding time periods. Individual health care providers can compare themselves with appropriately developed benchmarks for self-analysis and quality improvement. Similar analysis can be used to compare data from medical centers in other locations in the city, state, and country. Time series analysis of the same data can be used to establish analysis of process control. Time series analysis can also be used for predictive scheduling of materials and personnel, to plan for peak and trough demand on surgical services.

I. Diagnostic and Procedure Codes

Diagnostic codes, such as ICD-9 (International Classification of Diseases, 9th Revision), are stored in the database and are assigned to categorize the patients on admission and subsequently modified as new information becomes available, during surgery, for instance. Procedure codes such as CPT can be defined in the database and are assigned by health care providers at the time of surgery. Comparing diagnoses before, during, and after surgery or comparing similar diagnostic or therapeutic procedures indicates false positives, false negatives, and the relative prevalence of various medical conditions or procedures. These data can be made available to health care providers and managers to assist with quality improvement.

J. User-Friendly Interface

A mouse-driven "click and drag" graphic interface is used to make the system accessible, intuitive, and easy to use. Site-specific work sheets are created to display data in formats familiar to users and reduce change anxiety. Interface design, as much art as science, can be customized based on locally used charts and forms, for example, to make the screens as familiar as possible to the users.

K. Data Maintenance and Veracity

FIG. 6 is an information screen for the surgical intensive care unit. Note that the screen provides access to the names and numbers of all persons responsible for patient care in the intensive care unit. Expected admissions and discharges are posted for the benefit of health care providers in the unit and without. As a result, many providers having input into major decisions affecting a patient's discharge from a unit can have available to them all the information necessary to make an informed decision.

The data display screens at each location are designed according to existing work sheets and user interviews. Each geographic location bears responsibility for the maintenance and veracity of its own data. The data subset that each group of health care workers is responsible for is small, manageable, and relevant to its own work (see screen for the intensive care unit, FIG. 6). Because data entry is automated (bar code entry of time stamps from network time servers), it is easy to maintain accurate records. Also, because much of the patient identification data is inherited, the data are not likely to be compromised by errors associated with repetitive re-entry. Users who do not own data can view but not edit it. They can, however, call the appropriate persons with data ownership and request correction of any errors, which contributes to quality improvement.

L. Telephone Communications

To assist providers in communicating, each work station optionally can be combined with telephone and fax communications using modems or intercoms. Users who are consulting remote screens can establish voice or fax communications with those locations by selecting the appropriate telephone numbers from a directory which the computer can dial.

M. Duplication of Effort

By checking the progress of patients and work by networked computer, health care providers can reduce trips and phone calls to other geographic locations and reduce duplication of effort.

N. On-Line Data Analysis

An on-line graphic utilization review module is customized for each location in surgical services. The reports are initiated from a pull-down menu. Dialogue boxes allow searches by time interval and text strings, and the data can be sorted by demographic fields. For operating room utilization data, for example, there are both numeric (FIG. 7) and graphic (FIG. 8) utilization displays.

Each display summarizes three operating room time categories: available time (OR block time or staffed periods); scheduled time (patient surgery reservations); and used time (as recorded by bar code). In addition, utilization statistics are summarized as the following ratios:

$$\text{Actual utilization} = \frac{\text{used}}{\text{available}} \quad 1)$$

$$\text{Accuracy of utilization} = \frac{\text{scheduled}}{\text{used}} \quad 2)$$

$$\text{Forecast utilization} = \frac{\text{scheduled}}{\text{available}} \quad 3)$$

Figure 7:
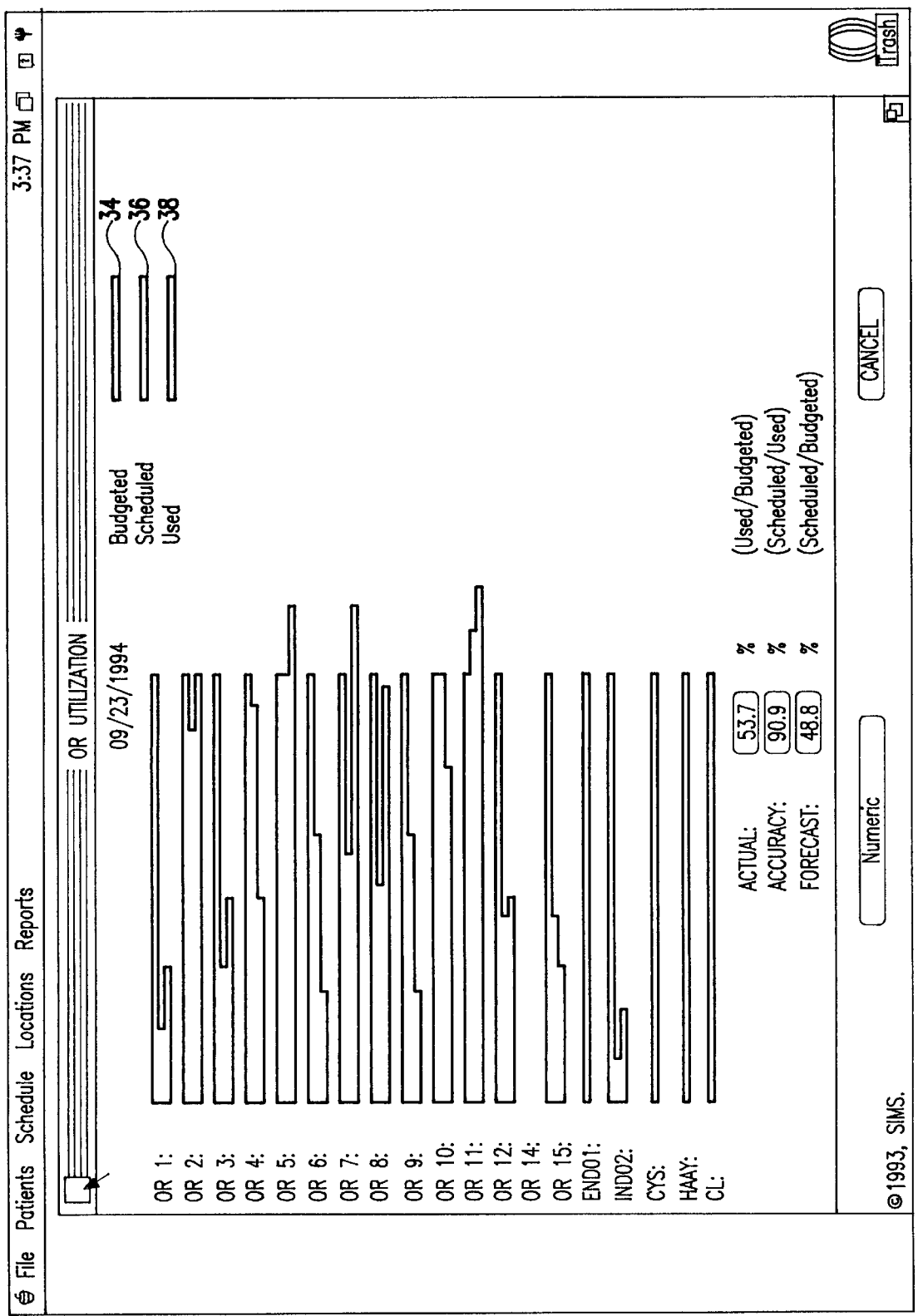
FIG. 7 is a graphic utilization review screen showing a histogram summary of budgeted (open bar), scheduled (textured bar), and used (filled bar) operating room utilization times for each operating room.

FIG. 7 is a graphic utilization review screen showing a histogram summary of budgeted 34 (open bar), scheduled 36 (textured bar), and used 38 (filled bar) operating room utilization times for each operating room. Actual, accuracy, and forecast utilization are computed as grand means for all operating rooms taken together.

FIG. 8 is a numerical utilization review screen (the numerical counterpart of FIG. 7) consisting of a matrix displaying three categories of time (budgeted, scheduled, used) and three summary utilization statistics (actual, accuracy, and forecast) for each operating theater. By highlighting each summary cell in the matrix and clicking on it, users can display details of the entire list of cases contributing to each summary cell in the matrix.

Pop-out boxes detail case duration for used, scheduled, and forecast times using graphic and numeric utilization (FIG. 9). Numeric and analytical on-line reports can be customized to accommodate specific users. On-line reports can be written to the screen, disc, or printer. FIG. 9 is a graphic utilization review screen pop-out feature giving access to details of case duration and starting times both scheduled 42 and used 44.

O. Report Writing

The bulk of custom report writing is accomplished by criteria-specific data searches and sorting to capture data which can be written to ASCII files for analysis outside of the present invention. The required records can be recalled using a transaction register utility (FIG. 10), allowing users to configure the searches and sorts from dialogue boxes, which can be used to specify time frame, text strings, and sorting criteria. FIG. 10 is a transaction register with selection 46 and sort buttons 48 for extracting data on-line.

VI. Specific Architecture

FIG. 12 shows the architecture of the present invention, consisting of five modules, some of which are accessible through their own graphic interface 60.

According to the features of the present invention, intelligent communication support over a peer-to-peer network linking the facilities listed in FIG. 1. System Status 62, Scheduling Manager 64, and a Calendar 66 are integrated using graphic interface 60. Two other modules, a Report Writer 68 and a Data Archive and Analyzer 70, 72, can be accessed directly (FIG. 12).

A. Report Writer

The report writer 68 provides hard-copy digests of performance and utilization and exception reports on either a scheduled or on-demand basis from various perspectives. Users provide "boilerplate" format for those reports; the present invention does not include natural language capabilities.

B. Data-Archive Analyzer

The data archive utility 70 stores records of surgical services provided. The data analyzer 72 performs routine analyses for the report writer 68 and real-time scheduler, and enables the user to extract raw data as desired.

C. Transaction Receipts

Figure 11:
FIG. 11 is a health care transaction receipt, according to an embodiment of the present invention.
Figure 13:
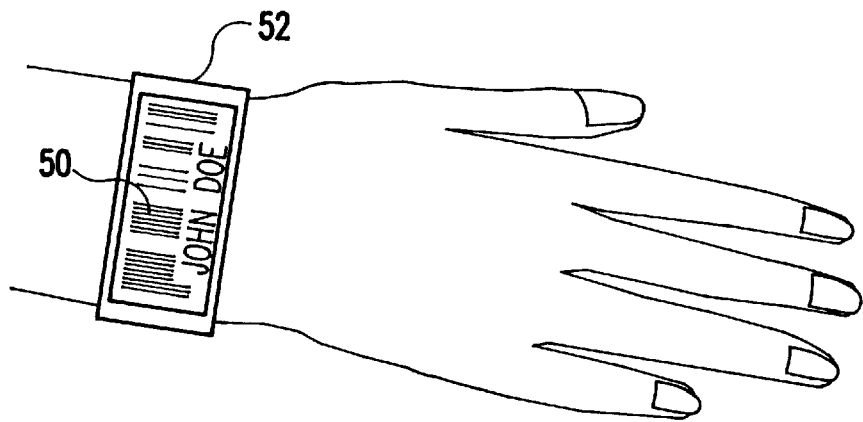
FIG. 13 is a bar code identification strip used in an embodiment of the present invention.

Residence and procedure times are tracked and recorded using, for example, bar codes. A typical bar code 50, such as that used by a preferred embodiment of the present invention to identify, for example, a patient receiving services, is shown in FIG. 13. The bar code may be attached to the patient's wrist using a strap 52. An audit trail is established for each patient and can be recalled on demand to study the time course and geographic progression of patients through surgical services. Procedure and diagnostic codes, together with the names of important health care providers such as the surgeon, anesthesiologist, and discharge nurse can be combined with residence and procedure times to produce a reconfigured audit trail known as a health care transaction receipt. This receipt (FIG. 11) is analogous to that from an automated teller machine. It provides details of a patient's surgery and hospital stay, together with provider contacts at the medical center. The receipt provides patients with a written record detailing their hospital treatment and the main contact persons from whom they received care. The receipt verifies subsequent hospital bills, strengthens the provider-patient contract, and provides the naive patient with a record of treatment in the event of an emergency.

D. Calendar

The calendar feature provides the predictive scheduler with the information necessary to schedule patients in advance. The calendar is linked to admissions and could be connected to other systems to download patient data and scheduling services.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A computer-based surgical services management system for tracking, recording, and communicating patient movement between site locations of a surgical services facility, the system comprising:

a peer-to-peer network including:
  a computer workstation located at each site location; and
  a coordinating server in network communication with each workstation;
a set of objects stored on the peer-to-peer network, all data relevant to an instance of an object being stored only in a distributed, non-relational database, the set of objects comprising:
  data objects for tracking and recording the patient movements and for producing patient-specific audit trails, the data objects and editing rights to the patient-specific audit trails moving from site to site with the patient; and
  site-specific data objects produced at each site location for storing site-specific data, the site-specific data objects being maintained at the site where the site-specific data is produced; and
an object-based application interface distributed on the peer-to-peer network for accessing, manipulating, and displaying the data objects, the data being stored only in the distributed, non-relational databases, by means of object-based methods specified by the distributed application,
wherein a copy of the set of objects is maintained in the coordinating server, data editing of objects being updated via object-based methods periodically over the peer-to-peer network.

2. The system of claim 1, wherein the database further comprises classes for patients, locations, resources, surgeons and anesthesiologists.

3. The system of claim 2, wherein methods are assigned to each of the classes for updating information.

4. The system of claim 2, wherein methods are assigned to perform constraint propagation in the network to maintain data structure.

5. The system of claim 1, wherein the object-based application interface further comprises a plurality of modules for maintaining and displaying the data objects, each of the plurality of modules being selected from the group consisting of:
  a system status module;
  a scheduling manager;
  a calendar;
  a report writer; and
  a data archive and analyzer.

6. The system of claim 1, further comprising a graphical interface for accessing selected ones of the plurality of modules in the database.

7. The system of claim 1, wherein the server comprises a selected number of workstations.

8. The system of claim 1, wherein workstation locations are selected from the group comprising:
  patient homes;
  same day surgery facilities;
  holding areas;
  operating rooms;
  postanesthesia care units;
  intensive care units; and
  hospital ward floors.

9. The system of claim 1, wherein the server is in network communication with each workstation using a network comprising a 10 Base T ethernet using either TCP/IP or Ethertalk protocols.

10. The system of claim 1, wherein the network further comprises repeaters for reading data from the distributed database and presenting the data to the user.

11. The system of claim 1, wherein the network further comprises a modem for remote access to the database.

12. The system of claim 1, further comprising security access controls and password protection for ensuring patient and hospital privacy.

13. The system of claim 1, wherein the database further comprises:
  personnel data for maintaining information regarding personnel, the personnel comprising surgeons, anesthesiologists, and nurses; and
  equipment data for maintaining information regarding equipment used in relation to surgical services.

14. The system of claim 1, wherein information is written to text file to generate a transaction register.

15. The system of claim 1, further comprising:
  means for inputting bar code information representing data specific to each patient;
  means for providing time-of-day information; and
  means for running a computer-based application for combining the bar code information and the time-of-day information to track and record residence and procedure times to produce an audit trail relative to a time course and geographic progression of a patient through surgical services, and whereby a transaction receipt is produced representing a written record for each patient of surgical services provided and who provided them.

16. The system of claim 1, further comprising:
  utilization screens for locations in surgical services; and
  time categories for locations in surgical services and displayed numerically or graphically on the utilization screens, the time categories being selected from the group consisting of:
  available time,
  scheduled time, and
  actual time,
  whereby actual utilization=actual time/available time, efficiency of utilization=scheduled time/actual time, and forecast utilization=scheduled time/available time.

17. The system of claim 1, wherein each workstation has a local hard disk memory device.

18. A computer-implemented method of managing data and for tracking, recording and communicating patient movement between site locations of a surgical services facility, the method comprising the steps of:
  establishing a set of objects in which all relevant data relevant to an instance of an object exclusively are stored, the set of objects comprising:

data objects for tracking and recording the patient movements and for producing patient-specific audit trails, the patient-specific audit trails having data editing rights; and site-specific data;

storing the set of objects in a distributed, non-relational database on a peer-to-peer computer network comprising individual workstations, selected ones of the workstations being located at each of the various site locations, a copy of the database being contained on each of the individual workstations, and a copy of the database contained on each of the individual workstations being contained in a coordinating server, the editing rights of the patient-specific data objects moving from site to site with the patient; and using an object-based application interface distributed on the peer-to-peer computer network to access, manipulate, and display the data objects stored only in the distributed, non-relational database, a copy of the set of objects being duplicated on the coordinating server, changes to the data objects being updated over the network on a periodic basis.

19. Apparatus for use in a computer-based surgical services management system for tracking, recording, and communicating patient movement between site locations of a surgical services facility, the system including a peer-to-peer network having a memory, a computer workstation located at each site location, and a coordinating server in network communication with each workstation, the apparatus comprising:

an object-based application interface distributed on the peer-to-peer network for accessing, manipulating, and displaying the data object, the data being stored only in the distributed, non-relational database, by means of object-based methods specified by the distributed application, wherein a copy of the object is maintained in the coordinating sever, data editing of object being updated via object-based methods periodically over the peer-to-peer network;

patient class information stored in the memory, the patient class information including:

data storage container definitions for defining data storage containers for holding an expected patient services path, an actual patient services path, patient demographics, and health care providers, respectively; and methods for updating information held in the data storage containers; and location class information stored in the memory, the location class including:

data storage container definitions for defining a data storage container for holding patient data and personnel data; and methods for updating information held in the data storage containers.

20. The apparatus of claim 19, further comprising resource class information including data storage container definitions for defining data storage containers for holding surgical services resource data.

21. The apparatus of claim 19, further comprising surgeon class information including data storage container definitions for defining data storage containers for holding surgeon data.

22. The apparatus of claim 19, wherein the patient class information further includes data storage container definitions for defining data storage containers for holding scheduled times for significant events along the path, expected durations for significant events along the path, actual times for significant events along the path, and actual durations for significant events along the path, respectively.

23. The apparatus of claim 19, wherein the patient class information further includes data storage container definitions for defining data storage containers for holding initial patient status, patient consent, and at least one interim patient status, respectively.

24. A computer program product for use in a computer-based surgical services management system for tracking, recording, and communicating patient movement between site locations of a surgical services facility, the system including a peer-to-peer network having a memory, a computer workstation located at each site location, and a coordinating server in network communication with each workstation, the computer program product comprising a computer usable medium having computer readable program code thereon including:

an object based application for distribution on the peer-to-peer network for accessing, manipulating, and displaying data object wherein the data being stored only in a distributed, non-relational database, by means of object-based method;

patient class information, the patient class information including:

data storage container definitions for defining data storage containers for holding an expected patient services path, an actual patient services path, patient demographics, and health care providers, respectively; and methods for updating information held in the data storage containers; and location class information, the location class including:

data storage container definitions for defining a data storage container for holding patient data and personnel data; and methods for updating information held in the data storage containers.

25. The computer program product of claim 24, further comprising program code for resource class information including data storage container definitions for defining data storage containers for holding surgical services resource data.

26. The computer program product of claim 24, further comprising program code for surgeon class information including data storage container definitions for defining data storage containers for holding surgeon data.

27. The computer program product of claim 24, wherein the patient class information further includes data storage container definitions for defining data storage containers for holding scheduled times for significant events along the path, expected durations for significant events along the path, actual times for significant events along the path, and actual durations for significant events along the path, respectively.

28. The computer program product of claim 24, wherein the patient class information further includes data storage container definitions for defining data storage containers for holding initial patient status, patient consent, and at least one interim patient status, respectively.

* * * * *